United States Patent [19]
Byng et al.

[11] Patent Number: 4,917,999
[45] Date of Patent: Apr. 17, 1990

[54] OLIGONUCLEOTIDE PROBES FOR DETECTION OF α-AMYLASE GENES

[75] Inventors: Graham Byng, Bristol; Karen L. Wollweber, Elkhart, both of Ind.

[73] Assignee: Miles Inc., Elkhart, Ind.

[21] Appl. No.: 902,905

[22] Filed: Sep. 2, 1986

[51] Int. Cl.$^4$ ............ C12Q 1/68; C07H 19/073; C07H 19/173
[52] U.S. Cl. ............................... 435/6; 536/27; 536/28; 536/29; 435/5; 435/7; 935/77; 935/78
[58] Field of Search ............... 935/77, 78; 435/5, 6, 435/7; 536/22, 28, 29

[56] References Cited
PUBLICATIONS

Takkinen et al., J. Biol. Chem., v. 258, pp. 1007–1013, 1983.

*Primary Examiner*—Ronald W. Griffin
*Assistant Examiner*—L. Eric Crane
*Attorney, Agent, or Firm*—E. P. Gray; M. G. Boguslaski

[57] ABSTRACT

Methods and compositions are provided for detecting a gene encoding α-amylase from a nucleic acid sample suspected of containing said gene. Said methods utilize oligonucleotide probes of consensus sequences deduced from highly conserved DNA sequences of various Bacillus species.

6 Claims, No Drawings

OLIGONUCLEOTIDE PROBES FOR DETECTION OF α-AMYLASE GENES

BACKGROUND OF THE INVENTION

α-Amylases are a group of enzymes capable of hydrolyzing the α-1,4 glucosidic bonds of starch polymers. Various such amylases have been identified from divergent sources such as fungi, bacteria, plants and mammals. These enzymes are distinct from the others in that they may exhibit different pH optima, thermostabilities, calcium ion requirements, and the like. Such variations are believed to be due to the primary, secondary and tertiary structures of the enzyme, per se.

Because of the prevalence of these enzymes and their industrial importance a general method for identifying the presence of a gene encoding an α-amylase would be of substantial utility. This is particularly true where little or no information is available pertaining to the physical structure of the enzyme believed to be produced or when the organism in question does not produce sufficient amounts of the α-amylase to be detected or identified by standard screening procedures which are used for natural isolates of new enzymes. The present invention is directed to such a method whereby oligonucleotide probes of consensus DNA sequences are used to hybridize specifically to, and thereby identify, genes encoding α-amylase from a variety of sources.

DESCRIPTION OF PERTINENT ART

All patents and publications cited in this document are expressly incorporated herein by reference.

It is known from the literature that α-amylases derived from *Aspergillus oryzae*, Bacillus species, barley, pig and mouse share three conserved protein domains based on the amino acid sequences of the enzymes, while the other regions of the enzymes differ in their primary structure (i.e., amino acid sequence). Two of these conserved domains consist of 12 amino acids each and may be part of the active site of each enzyme. Rogers, J. C. *Biochem. Biophys. Res. Comm.*, 128:1, pp. 470-476 (1985) and Ihara et al, *J. Biochem.*, 98:1, pp. 95-103 (1985). Both authors describe the importance of their findings for elucidating the evolutionary relationships among these species.

Further, Pace et al, *ASM News*, 5181, pp. 4-12 (1985) describe techniques used in analyzing the phylogenetic relationships of mixed, naturally occurring microbial populations. In this approach, probes are prepared which are complementary to the genomic DNA coding for the 16s subunit of ribosomal RNA. The probe is said to be a "mixed kingdom" probe and is composed of highly conserved RNA sequences found in all organisms tested. The probe was then used to detect all 16s ribosomal RNA sequences present in a given microbial population for purposes of determining their evolutionary relatedness. The strategy for using the 16s ribosomal RNA sequences as generalized probes derives from the fact that these sequences ultimately direct the process of protein translation within cells. Since this process is universal and essential for life, the molecules which participate in this process have remained essentially unchanged in all organisms.

None of the above-cited references describes or suggests the production of oligonucleotide probes capable of identifying α-amylase genes in various organisms or to identify organisms which produce α-amylases.

SUMMARY OF THE INVENTION

The present invention is directed to oligonucleotide probes for use in the detection of a gene encoding an α-amylase in an organism suspected of carrying said gene. One such probe is an oligonucleotide having a base sequence of sufficient complementarity to hybridize, under hybridization conditions, with a second base sequence present in the organisms *Bacillus stearothermophilus*, *Bacillus subtilis* NA64, *Bacillus amyloliquefaciens*, and *Bacillus licheniformis*, said second base sequence encoding the amino acid sequence asp-gly-phe-arg-leu-asp-ala-val-lys-his-ile. A second such probe is similarly an oligonucleotide having a base sequence of sufficient complementarity to hybridize, under hybridization conditions, with a second base sequence present in the above-noted Bacillus organisms, said second base sequence encoding the amino acid sequence val-thr-phe-val-asp-asn-his-asp-thr.

Also disclosed are methods for detecting the presence of a gene encoding the enzyme α-amylase in an organism suspected of containing said gene. The method is carried out by contacting an oligonucleotide probe of the present invention with a DNA sample from said organism under conditions favorable to hybridization between said probe and said sample and determining the presence of hybridized probe.

DETAILED DESCRIPTION OF THE INVENTION

The oligonucleotide probes of the present invention (probes Amy-1 and Amy-2) represent deduced consensus sequences from two highly conserved domains from previously cloned α-amylases from the genus Bacillus. See Table I.

TABLE I (Probe Amy-1)

| Strain | Amino Acid Numbers | Reference | asp | gly | phe | arg | leu | asp | ala | val | lys | his | ile |
|---|---|---|---|---|---|---|---|---|---|---|---|---|---|
| B. stearothermophilus | 229-239 | 1 | GAT | GGG | TTC | CGG | CTT | GAT | GCC | GTC | AAG | CAT | ATT |
| B. subtilis NA64 | 171-181 | 2 | GAC | GGT | TTT | CGA | TTT (phe) | GAT | GCC | GCC (ala) | AAA | CAT | ATA |
| B. amyloliquefaciens | 226-236 | 3 | GAC | GGG | TTC | CGT | ATT (ile) | GAT | GCC | GCC (ala) | AAA | CAT | ATT |
| B. licheniformis | 226-236 | 4 | GAC | GGT | TTC | CGT | CTT | GAT | GCT | GTC | AAA | CAC | ATT |
| Probe Amy-1: | | | GAI | GGI | TTI | CGI | ITT | GAT | GCC | GIC | AAI | CAT | ATT |

(wherein I represents inosine)

(Probe Amy-2)

Amino                                Sequence

TABLE I-continued

| Strain | Acid Numbers | Reference | val | thr | phe | val | asp | asn | his | asp | thr |
|---|---|---|---|---|---|---|---|---|---|---|---|
| B. stearothermophilus | 324–332 | 1 | GTC | ACC | TTC | GTT | GAT | AAT | CAT | GAC | ACC |
| B. subtilis NA 64 | 263–271 | 2 | GTG | ACA | TGG (trp) | GTA | GAG (glu) | TCG (ser) | CAT | GAT | ACG |
| B. amyloliquefaciens | 321–329 | 3 | GTT | ACA | TTT | GTT | GAA (glu) | AAT | CAT | GAC | ACA |
| B. licheniformis | 321–329 | 4 | GTT | ACA | TTT | GTC | GAT | AAC | CAT | GAT | ACA |
| Probe Amy-2: | | | GTT | ACA | TTT | GTT | GAA | AAT | CAT | GAC | ACA |

References:
1 Nakajima et al, J. Bact., 163, 401–406 (1985)
2 Yamazaki et al, J. Bact., 156:1 327–337 (1983)
3 Takkinen et al, J. Biol. Chem., 258, 1007–1013 (1983)
4 Toshifumi et al, J. Biochem., 98, 1147–1156 (1985)

As can be seen from Table I, probe Amy-1 is 33 nucleotides in length and contains 7 inosine moieties at positions of ambiguity. The consensus sequence was deduced from four previously cloned α-amylase genes from amino acid numbers 229–239 of *Bacillus stearothermophilus* (Nakajima, et al, *J. Bact.* 163, pp. 401–406, 1985); amino acid numbers 171–181 of *Bacillus subtilis* NA64 (Yamazaki, et al, *J. Bact.* 156:1, pp. 327–337, 1983); amino acid numbers 226–236 of *Bacillus amyloliquefaciens* (Takkinen, et al, *J. Biol. Chem.*, 258, pp. 1007–1013, 1983); and amino acid numbers 226–236 of *Bacillus licheniformis* (Toshifumi, et al, *J. Biochem.*, 98, 1147–1156, 1985). The domain encoded by each of these four regions is the amino acid sequence: aspartic acid-glycine-phenylalanine-arginine-leucine-aspartic acid-alanine-valine-lysine-histidine-isoleucine. This sequence is shown in Table I in its conventional three-letter nomenclature. The use of inosine at positions of ambiguity has been previously reported and does not adversely affect the use of said probes in the method of the present invention. See *Nucleic Acids Research*, Vol. 13, No. 24, pp. 8927–8938, 1985, "Base Pairing Involving Deoxyinosine: Implications for Probe Design", Francis H. Martin, Miguel M. Castro and *Journal of Bioloqical Chemistry*, Vol. 260, No. 5, pp. 2605–2608, 1985, "An Alternative Approach to Deoxyoligonucleotides as Hybridization Probes by Insertion of Deoxyinosine at Ambiguous Positions", Eiko Ontsuka, Shigeru Matsuki, Morio Ikehara, Yoosuke Takahasi, Henichi Matsubara. Similarly, probe Amy-2 is 27 nucleotides in length and is a deduced consensus sequence from a highly conserved region present in each of the four Bacillus species denoted above: amino acid numbers 324–332 of *Bacillus stearothermophilus* (Nakajima, et al, supra); amino acid numbers 263–271 of *Bacillus subtilis* NA64 (Yamazaki, et al, supra); amino acid numbers 321–329 of *Bacillus amyloliquefaciens* (Takkinen, et al, supra); and amino acid numbers 321–329 of *Bacillus licheniformis* Toshifumi, et al, supra). The domain encoded by each of these four regions is the amino acid sequence: valine-threonine-phenylalanine-valine-aspartic acid-asparagine-histidine-aspartic acid-threonine. This sequence is also shown in Table I in its conventional three-letter nomenclature. The nucleotide sequence abbreviations shown in Table I are, of course, those of convention; wherein G represents guanine, A represents adenine, T represents thymine, and C represents cytosine. As noted earlier, inosine substitutions were made at positions of ambiguity in probe Amy-1 and these substitutions are represented by the letter I.

Being consensus sequences, probes Amy-1 and Amy-2 have the capacity to hybridize with α-amylase genes in bacteria and other organisms whose amylases are uncharacterized and/or for which no genetic analyses currently exist. Thus, these probes may be used to identify the α-amylase gene of interest in a particular organism or to identify an amylase producing organism from a population of non-producing organisms. Further, the use of these probes to clone amylase genes and to screen a gene bank represents a significant improvement over conventional methodologies such as the construction of a probe based on the deduced nucleotide sequence following determination of the amino acid sequence of a purified protein. The use of probes Amy-1 and Amy-2 requires no knowledge of the structure of the particular amylase of interest in order to carry out the screening of a gene bank, for example. In addition, it may be possible to use probes Amy-1 and Amy-2 to determine the active site of a particular amylase, and allow for subsequent modification of this location by in vitro site-directed mutagenesis.

Owing to the fact that the nucleotide sequence of probes Amy-1 and Amy-2 are known, chemical synthesis of said probes may be carried out by conventional techniques. Such techniques include, for example, the phosphodiester method (Agarwal et al, Agnew, *Chem. Int. Ed. Engl.*, 11:451, 1972), phosphotriester method (Hsiung et al, *Nucleic Acids Res.*, 6:1371, 1979) and the phosphoramidite solid phase method. See, Matteucci, M. D. and Caruthers, M. H. [1981] *J. Am. Chem. Soc.* 103:3185 and Beaucage, S. L. and Caruthers, M.H. [1981] *Tetrahedron Lett.* 22:1859.

Probes Amy-1 and Amy-2 and functional derivatives thereof may be used as described herein. The term "functional derivatives" refers to nucleotide sequences substantially similar to those defined herein for probes Amy-1 and Amy-2 but which retain the capacity to hybridize with α-amylase genes. The skilled artisan will readily appreciate that modifications in the nucleotide sequence of probes Amy-1 and Amy-2 may be made, as by the deletion of one or more bases and the insertion therefor of a different base (i.e., adenine, guanine, cytosine or thymine) or a moiety such as inosine. Where such modification in the nucleotide sequence for probes Amy-1 and Amy-2 result in a nucleotide sequence (probe) which retains the functional capacity to hybridize with complementary regions of α-amylase genes in bacteria and other organisms, such a probe is a functional derivative of probes Amy-1 and Amy-2 and is a contemplated equivalent thereof.

Hybridization of said probe to sample nucleic acid containing a gene encoding an α-amylase is affected by the hybridization conditions chosen. That is to say, various parameters such as incubation time and temperature, probe:sample ratio, buffer and salt concentrations, and the like have a great influence on the degree of stability obtained in the formed duplex. The more stringent the parameters (i.e., low salt concentrations and higher temperatures, for example), the greater the degree of complementarity required for duplex formation (hybridization). On the other hand, it may be desirable to allow hybridization between less complementary sequences which may be achieved by lowering the stringency of the hybridization conditions as, for example, by lowering the temperature and increasing the ionic strength of the buffer. Further, probes Amy-1 and Amy-2 may be used simultaneously for hybridization with a DNA sample or may be used sequentially (in either order) or may by used alternatively for hybridization with and subsequent detection of an o-amylase gene from an organism suspected of containing said gene.

Practice of the present method is not limited to any particular hybridization format. The manner in which hybridization resulting between the probe and sample nucleic acids is determined is primarily a matter of convenience. Any conventional hybridization technique can be used. As improvements are made and as conceptually new formats are developed, such can be readily applied to carrying out the present method.

Conventional hybridization formats which are particularly useful include those wherein the sample nucleic acids or the oligonucleotide probe is immobilized on a solid support (solid-phase hybridization) and those wherein the probe and sample nucleic acids are all in solution (solution hybridization).

In a solid phase hybridization, one of the species participating in hybridization is fixed in an appropriate manner in its single stranded form to a solid support. Useful solid supports are well known in the art and include those which bind nucleic acids either covalently or noncovalently. Noncovalent supports which are generally understood to involve hydrophobic bonding include naturally occurring and synthetic polymeric materials, such as nitrocellulose, derivatized nylon, and fluorinated polyhydrocarbons, in a variety of forms such as filters or solid sheets. Covalent binding supports are also useful and comprise materials having a chemically reactive group or groups, such as dichlorotriazine, diazobenzyloxymethyl, and the like, which can be activated for binding to polynucleotides. Other supports include those which entrap the target DNA, such as agarose and polyacrylamide gels.

A typical solid-phase hybridization technique begins with immobilization of sample nucleic acids onto the support in single stranded form. This initial step essentially prevents reannealing of complementary strands from the sample and can be used as a means for concentrating sample material on the support for enhanced detectability. The oligonucleotide probe is then contacted, in a single stranded, labeled form, with the support. Appropriate labels are available by which to detect resulting hybridization on the support. A more detailed discussion of solid phase hybridization formats may be obtained from the following: Southern, E.M. (1975) "Detection of Specific Sequences Among DNA Separated by Gel Electrophoresis" *J. Mol. Biol.* 98:503-517; Grunstein, M.; Hogness D.S. (1975) "Colony Hybridization: A Method for the Isolation of Cloned DNAs that Contain a Specific Gene" *Proc. Natl. Acad. Sci.* USA 72:3961-3965; Wahl, G. M.; Stern, M.; Stark, G. R. (1979) "Efficient Transfer of Large DNA Fragments from Agarose Gels to Diazobenzyloxymethyl-Paper and Rapid Hybridization by Using Dextran Sulphate" *Proc. Natl. Acad. Sci.* USA 76:3683-3687; and Purrello, M. and Balzas, I. (1983) "Direct Hybridization of Labeled DNA to DNA in Agarose Gels" *Anal. Biochem.* 128:393-397.

In a solution format, the specimen nucleic acids are first released from the organism of interest by lysis, and then denatured. These steps may be combined by heating the sample to 100° C. or by exposing it to base. After adding a solution containing a large excess of the probe, hybridization is allowed to occur under conditions of ionic strength and temperature empirically determined to give the desired probe specificity and sensitivity.

Hybrids can be detected and quantified using a number of methods For example, after hybridization the remaining single stranded nucleic acid can be hydrolyzed into small fragments with the single strand specific nuclease $S_1$. Acid precipitation followed by centrifugation or filtration can be used to concentrate the hybrids and separate them from the hydrolyzed single-stranded nucleic acids. The amount of precipitate collected is then quantified. In another approach, hybridized and single-stranded oligonucleotides can be separated by chromatography on hydroxyapatite. Other solution methods are known and will be developed.

Probes Amy-1 and Amy-2 can be incorporated with a variety of labels which function to detect the presence of the hybridized duplex either qualitatively or quantitatively. Useful labels include radioisotopes as well as nonradioisotopic labels. Isotopic labels include, but are not limited to, $^3H$, $^{35}S$, $^{32}P$, $^{125}I$ and $^{14}C$. The method of radioactively labeling the probe or other material will depend upon its particular nature (e.g., RNA vs. DNA, single-stranded vs. double-stranded). Many labeling methods are enzymatic. These include, but are not limited to, the known methods of nick translation, end labeling, second strand synthesis, reverse transcription and transcription. All of these methods generally require the isotopically labeled nucleotides to function as enzyme substrates. Alternatively, a radiolabel can be incorporated into the oligonucleotide probe by chemical modification of the probe. This method is used most commonly with $^{125}I$ labels.

With a radiolabeled oligonucleotide probe, hybridization can be detected by autoradiography, scintillation counting or gamma-counting. The method used would depend upon the hybridization format, the type of test (qualitative or quantitative), and the radioisotope used as a label.

Nonradioisotopic materials can also be used as labels. Such labels can be incorporated into the polynucleotide probe or other material to be labeled by enzymatically incorporating modified nucleotides using one of the enzymatic procedures outlined above where the labeled nucleotides serve as enzyme substrates for the appropriate enzymes. Alternatively, a label could be introduced into an oligonucleotide probe by conventional chemical modifications of the probe.

Useful labels include, but are not limited to, haptens or other ligands, fluorescers, chemiluminescers, chromophores, and participants in enzymatic reactions (e.g., enzymes, enzyme cofactors, enzyme substrates, and enzyme modulators, e.g., inhibitors). These labels are detected on the basis of their own physical properties (e.g., fluorescers and chromophores) or their reactive properties (e.g., the others listed). For example, a cofactor-labeled probe can be detected by adding the enzyme for which the label is a cofactor and a substrate for the enzyme. A hapten and ligand labeled polynucleotide probe can be detected by adding an antibody to the hapten or a protein which binds the ligand, tagged with a detectable molecule. Such detectable molecule can be some molecule with a measurable physical property (e.g., fluorescence or absorbance) or a participant in an enzyme reaction (e.g., see above list). For example, one can use an enzyme which acts upon a substrate to generate a product with a measurable physical property. Examples of the latter include, but are not limited to, β-galactosidase, alkaline phosphatase and peroxidase. For in situ hybridization studies, ideally the final product is water insoluble.

In general, labels and labeling approaches which have been developed for use in immunoassays will be applicable to the present hybridization technique with modifications evident to the ordinary skilled worker. See U.S. Pat. Nos. 4,380,580; 4,279,992; 4,238,565; 4,134,792; 4,273,866; 3,817,837; 4,043,872; 4,238,195; 3,935,074; 3,998,943; 3,654,090; 3,992,631; 4,160,016; and 3,996,345; British Patent Specs. 1,552,607 and 3,019,408; and European Patent Appln. 70,687; 70,685; and 63,879. It will be clearly recognized that the present invention is not limited to any particular hybridization format or formats or particular labels. As new techniques and labels are developed, they will be applicable to the present method. Reference to *Molecular Cloning, A laboratory Manual*, T. Maniatis et al, Cold Spring Harbor Laboratory (1982) will provide additional details concerning nucleic acid hybridization.

The organism believed to be carrying a gene encoding an α-amylase may be treated in a variety of known ways in order to release the nucleic acid in single-stranded form therefrom. Release of nucleic acids can, for example, be obtained by mechanical disruption (freeze/thaw, abrasion, sonication), physical/chemical disruption (detergents such as Triton, Tween, sodium dodecylsulfate, alkali treatment, osmotic shock, heat-boiling water), or enzymatic lysis (lysozyme, mutanolysin). Denaturation of released nucleic acids is preferably accomplished by heating in boiling water or alkali treatment (e.g., 0.1 normal sodium hydroxide), which, if desired, can simultaneously be used to lyse the cells.

The following examples are provided as a means of illustrating the present invention and are not to be construed as a limitation thereon.

EXAMPLE 1

Detection of an αamylase gene in *Bacillus caldolyticus*

(a) Preparation of Probes Amy-1 and Amy-2

The oligonucleotide probes Amy-1 and Amy-2 were prepared using solid-phase synthetic methods (Alkinson et al, 1984). The scheme for synthesis of the oligomers was as outlined by Matteucci et al, supra (1981) utilizing proton activated, protected 2'-deoxy-ribonucleotide phosphoramidites (Beaucage et al, supra 1981). All sequential steps were performed in an automated manner on an Applied Biosystems Model 380 DNA Synthesizer using protected nucleotides, solvents, chemicals and reagents, all of which were obtained from Applied Biosystems, Foster City, Calif. U.S.A. The solid-phase support (also from Applied Biosystems) was controlled pore glass to which the starting 3'-nucleotide was already attached. Certain modifications were introduced into the automated reaction cycle in accordance with the manufacturer's recommendations. Upon completion of the synthesis, the oligomers were deblocked and cleaved from the solid support within the DNA synthesizer according to the manufacturer's recommendations.

Removal of the blocking groups was completed by heating the aqueous solution containing the oligomer with concentrated ammonium hydroxide at 55° centigrade (C) for from 4 to 24 hours in a sealed vial. The resulting solution was evaporated, the residue dissolved in 0.01 molar (M) triethylammonium bicarbonate buffer, pH 7.0 (TEAB buffer). This solution was chromatographed over Sephadex-G50® Gel Filtration Resin. This column was prepared in, and eluted with, the same TEAB buffer. Material eluting with the void volume was pooled and the solution evaporated. A portion of the residue (10 to 40% of the absorbance units at 260 nanometers), dissolved in loading buffer (composition: 0.1% Bromophenol Blue, 0.1% Xylene Cyanol, 10 millimolar disodium EDTA, in formamide) was further purified by electrophoresis on polyacrylamide gels. The gel size was 18×32 centimeters (cm) with a thickness of 1.5 millimeters (mm). The well size for each oligomer purified in this manner was 2 to 5 cm in width and up to five oligomers were purified using a single gel. The concentration of acrylamide in the gel varied from 14 to 20%, depending on the chain length of the desired product. For longer oligomers, the 14% gel is preferred, while shorter oligomers were purified on up to a 20% acrylamide gel. The gel also contained 7M urea and Tris-borate-EDTA buffer (0.1 M Tris, 0.1M borate, 2 millimolar EDTA, pH 8.3). The running buffer was the same Tris-Borate-EDTA mixture. Electrophoresis was carried out at 20 to 60 watts, constant power, for from 6 to 18 hours.

Following completion of the electrophoresis, the gel was encased in plastic wrap and the oligomers were visualized by shadowing with ultraviolet light. This shadowing was accomplished by placing the wrapped gel on a fluorescent thin layer chromatography plate and viewing the gel with a short wave length ultraviolet light source. The desired product appeared as the slowest migrating, major blue band by this shadowing technique. The desired band was excised from the gel. The DNA oligomer was eluted from the gel slice onto powdered diethylaminoethyl (DEAE) cellulose using an EpiGene (Baltimore, Md., U.S.A.) D-Gel® electrophoresis apparatus. The oligomer was recovered from the cellulose by elution with 1M TEAB buffer. The buffer solution containing the oligomer was evaporated, the residue dissolved in 0.01M TEAB buffer, and then desalted by passage over a column of Sephadex-G50® as described previously. The material eluting in the void volume was pooled and lyophilized to give the final product. Using these procedures, about 0.5 to 5.0 $A_{260}$ units of each of the purified oligomers was obtained.

(b) Radiolabeling of Probes Amy-1 and Amy-2

Each oligonucleotide probe (prepared as described in Example 1a) was radiolabeled in a reaction composed of the following: 0.02 $A_{260}$ units of DNA oligomer, 4.0 units of $T_4$ polynucleotide kinase (Boehringer-Mannheim), 2.5 microliter (μl) of a 10X Tris buffer (as recommended by the manufacturer), 200 microcurie (μCi) $\gamma-^{32}$-P adenosine triphosphate (ATP) supplied by Amersham in a total volume of 25 μl. The reaction was incubated at 37° C. for 30 minutes. Then 75 μl of 0.1X saline sodium citrate (SSC) buffer (1X SSC is 0.15M NaCl, 0.015M sodium citrate, pH 8.0) was added to stop the reaction. The mixture was passed through a 1.0 milliliter (ml) Sephadex G-50 column, which retained the unincorporated ATP. The eluant consisted of 100 μl of labeled oligonucleotide with a total activity of approximately $2.5 \times 10^8$ counts per minute (cpm), as determined by Cerenkov counting in a liquid scintillation counter.

(c) Detection of an α-amylase gene in *Bacillus caldolyticus*

A 250 ml nutrient broth culture of *Bacillus caldolyticus* was grown for 18 hours at 60° C. The cells were then washed in 0.1M sodium phosphate (pH 6.8) and then suspended in a buffer containing 20 millimolar (mM) sodium phosphate (pH 6.8), 1 mM $MgCl_2$ and 25 percent sucrose and then treated with 500 units mutanolysin (Sigma Chemical Co., St. Louis, Mo. U.S.A.) for 90 minutes at 50° C. The cells were then lysed by the addition of a detergent containing 1% Brij 58, 0.4% sodium deoxycholate, 0.062M ethylene-diaminetetraacetic acid (EDTA) and 0.05M Tris-HCl (pH 8.0). The lysed solution was then extracted once with an equal volume of water-saturated phenol and once with an equal volume of chloroform. The resultant aqueous phase was then made 0.3M in sodium acetate. Two volumes of 95% ethanol were added, resulting in the precipitation of the DNA. The DNA was resuspended in 0.1X SSC buffer and treated sequentially with RNAse (pancreatic, from Boehringer-Mannheim, 100 microgram (μg) per ml for 60 minutes at 37° C.) then protease K (Boehringer-Mannheim, 100 μg/ml for 60 minutes at 37° C). The resulting DNA was again extracted once with 1 volume of phenol and once with 1 volume of chloroform. The resulting DNA was then dialyzed against 10 mM Tris-HCl (pH 8.0), 1.0 mM EDTA (pH 8.0) and 0.1M NaCl and then against 10 mM Tris HCl (pH 8.0) and 1.0 mM EDTA.

1.0 μg aliquots of the DNA prepared as above were digested separately with the restriction endonucleases EcoRI, SalI, BamHI, BclI, PstI and AccI under the conditions recommended by the manufacturer (International Biotechnologies, Inc.). Each reaction was subjected to electrophoresis on two identical 0.8% agarose gels under conditions sufficient to separate the fragments, usually 5 volts/cm for 8 hours. The gels were then dried for one hour at 60° C. onto Whatman 3MM filter paper in a vacuum gel dryer. The dried gels were then soaked in a solution of 0.5 normal (N) NaOH, 0.15M NaCl for 30 minutes and then soaked again in 0.5M Tris-HCl (pH 8.0) for 1 hour at 0° C. Following this, the gels were then submerged in 0.25% non-fat dry milk in 2X SSC buffer for 1 hour at 65° C.

$5 \times 10^7$ cpm of each of the labeled probe Amy-1 and Amy-2 (prepared as in step b, above) were added separately to each of 10 ml aliquots of the non-fat dry milk solution described above. Each probe solution was then placed with a gel in a sealed plastic bag, using a separate bag for each probe and gel. The bag was incubated for 2 hours at 40° C. The gels were then removed and washed three times with 500 ml of 2X saline sodium citrate and 0.1% sodium dodecylsulfate at 45° C. The gels were then wrapped in plastic wrap and exposed to X-ray film (Kodak AR) for 48 hours at −70° C. The resulting autoradiograms revealed that both probes hybridized to specific bands in each restriction endonuclease digest of *Bacillus caldolyticus* DNA. (In some restriction digests, the size of the hybridizing bands was the same for probe Amy-1 and probe Amy-2, indicating that the particular enzyme did not cut the DNA at a position between the locations where these probes bind). Both probes also hybridized to an α-amylase gene cloned from *Bacillus licheniformis* (as described in Example 2) but not to bacteriophage lambda DNA, evidencing the identification of an α-amylase gene from *Bacillus caldolyticus*.

EXAMPLE 2

Detection of an α-amylase gene in *Bacillus licheniformis*

*Bacillus licheniformis* produces an amylase which has been characterized as a true α-amylase (Chiang et al, *Starch*, 31:3, 86–92, 1979). The α-amylase gene from this organism has been previously cloned, said clone consisting of a 3.5 kilobase EcoR1 fragment on the vector plasmid pUB110 which directs the synthesis of α-amylase when introduced into a strain of *Bacillus subtilis* which does not normally produce this protein. Probes Amy-1 and Amy-2 were prepared as described in Examples 1a and 1b. The hybridization was conducted as described in Example 1c. Probes Amy-1 and Amy-2 were found to hybridize to the cloned α-amylase gene (at 45° C.) but not to the DNA from the vector plasmid pUB110, and also to hybridize specifically to *Bacillus licheniformis* genomic DNA (at 45° C.). This result indicates that probes Amy-1 and Amy-2 are hybridizing to DNA encoding the α-amylase gene of *Bacillus licheniformis* itself and not coincidentally to unrelated DNA of this strain.

EXAMPLE 3

Detection of an amylase gene in *Bacillus alkalophilus*

Using the radiolabeled probes Amy-1 and Amy-2 (prepared as described in Examples 1a and 1b), an amylase gene was detected in *Bacillus alkalophilus* subspecies halodurans. The DNA was released from the cells by treatment with lysozyme and the hybridization was otherwise as conducted in Example 1c (except for incubation of the probes and gels at 35° C. and subsequent washing of the gels at 40° C.). The resulting autoradiogram revealed hybridized probe to the amylase gene. The amylase produced by this organism is believed to be an endo-acting amylase producing substrate degradation products in the β-configuration. See Boyer et al, *Starch*, 31, 166–171 (1979). This suggests that probes Amy-1 and Amy-2 may also have utility in identifying genes encoding α-amylase-like enzymes such as that produced by *Bacillus alkalophilus* subspecies *halodurans* which cannot be classified as true α- or true β-amylases.

EXAMPLE 4

Detection of an α-amylase gene in *E. coli*

An α-amylase produced by *E. coli* has been reported by Freundlieb and Boos (*J. Biol. Chem.*, 261, No. 6, 2946–2953, 1986). Using the radiolabeled probe Amy-1 (prepared as described in Examples 1a and 1b), an α-amylase gene was detected in *E. coli*. The methodologies of Example 1c were used except that lysozyme was used to release the DNA from the cells.

What is claimed is:

1. An oligonucleotide probe for use in the detection of a gene encoding α-amylase in an organism suspected of carrying the gene, comprising:
   an oligonucleotide having a base sequence chosen from the sequences,
   (a) GAI GGI TTI CGI ITT GAT GCC GIC AAI CAT ATT
      wherein I is inosine; or
   (b) GTT ACA TTT GTT GAA AAT CAT GAC ACA which oligonucleotides are capable of hybridization, under hybridization conditions, with a second base sequence present in the organisms *Bacillus stearothermophilus, Bacillus subtilis* NA64, *Bacillus amuloliquefaciens* and *Bacillus licheniformis,* which second base sequence is capable of encoding the aminoacid sequence asp-gly-phe-arg-leu-asp-ala-val-lys-his-ile.

2. The oligonucleotide probe comprising the sequence:

(a) GAI GGI TTI CGI ITT GAT GCC GIC AAI CAT ATT wherein I is inosine; or the sequence (b) GTT ACA TTT GTT GAA AAT CAT GAC ACA.

3. A method for detecting the presence of a gene encoding the enzyme α-amylase from an organism suspected of containing said gene comprising contacting the oligonucleotide probe of claim 1 with a DNA sample from said organism under conditions favorable to hybridization between said probe and said sample and determining the presence of hybridized probe.

4. A method for detecting the presence of a gene encoding the enzyme α-amylase from an organism suspected of containing said gene comprising contacting an oligonucleotide probe of the sequence:

GAI GGI TTI CGI ITT GAT GCC GIC AAI CAT ATT wherein I is inosine with a DNA sample from said organism under conditions favorable to hybridization between said probe and said sample and determining the presence of hybridized probe.

5. A method for detecting the presence of a gene encoding the enzyme αamylase from an organism suspected of containing said gene comprising contacting the oligonucleotide probe of claim 2 with a DNA sample from said organism under conditions favorable to hybridization between said probe and said sample and determining the presence of hybridized probe.

6. A method for detecting the presence of a gene encoding the enzyme α-amylase from an organism suspected of containing said gene comprising contacting an oligonucleotide probe of the sequence:

GTT ACA TTT GTT GAA AAT CAT GAC ACA with a DNA sample from said organism under conditions favorable to hybridization between said probe and said sample and determining the presence of hybridized probe.

* * * * *